(12) United States Patent
Beya et al.

(10) Patent No.: US 8,347,745 B2
(45) Date of Patent: Jan. 8, 2013

(54) COUNTING INCLUSIONS IN ALLOYS BY IMAGE ANALYSIS

(75) Inventors: William Beya, Villetaneuse (FR); Marie Cuoco, Viry Chatillon (FR); Marie-Noelle Hinard, Bondoufle (FR); Beatrice Peltier, Brunoy (FR)

(73) Assignee: SNECMA, Paris (FR)

( * ) Notice: Subject to any disclaimer, the term of this patent is extended or adjusted under 35 U.S.C. 154(b) by 91 days.

(21) Appl. No.: 13/126,173

(22) PCT Filed: Oct. 27, 2009

(86) PCT No.: PCT/FR2009/052066
§ 371 (c)(1),
(2), (4) Date: Apr. 27, 2011

(87) PCT Pub. No.: WO2010/049640
PCT Pub. Date: May 6, 2010

(65) Prior Publication Data
US 2011/0204227 A1    Aug. 25, 2011

(30) Foreign Application Priority Data
Oct. 27, 2008 (FR) ...................... 08 57268

(51) Int. Cl.
*G01N 33/00* (2006.01)
(52) U.S. Cl. ........................................ 73/866
(58) Field of Classification Search ........................ None
See application file for complete search history.

(56) References Cited

U.S. PATENT DOCUMENTS

| | | | |
|---|---|---|---|
| 4,560,872 A | 12/1985 | Antonovsky | |
| 6,432,718 B1 * | 8/2002 | Umezawa et al. | 436/177 |
| 6,803,235 B1 | 10/2004 | Mize et al. | |
| 2003/0130806 A1 * | 7/2003 | Mizuno et al. | 702/35 |

FOREIGN PATENT DOCUMENTS

JP    61 62849    3/1986

OTHER PUBLICATIONS

Spitzig, W.A.; et al. "SEM-Based Automatic Image Analysis of Sulfide Inclusions in Hot-Rolled Carbon Steels." Metallography, vol. 16, No. 2. pp. 171-198. XP024401904 (May 1, 1983).
International Search Report issued Jan. 18, 2010 in PCT/FR09/52066 filed Oct. 27, 2009.

* cited by examiner

*Primary Examiner* — Robert Raevis
(74) *Attorney, Agent, or Firm* — Oblon, Spivak, McClelland, Maier & Neustadt, L.L.P.

(57) ABSTRACT

A method of counting and analyzing an alloy by image analysis. The method includes a) preparing a sample of the alloy; b) determining inclusion detection thresholds by observation, with magnification, of at least one field of the sample; c) detecting inclusions of the sample as a function of the threshold defined in b), and counting the inclusions; d) acquiring images of each of the inclusions detected in c) and determining a size of each of the inclusions; e) determining the chemical composition of each of the detected inclusions by chemically analyzing each of them; and f) making a map of the sample from the images acquired in d), the map showing spatial distribution of the inclusions, in which each of the detected inclusions is represented by a graphics element, a size of the graphics element being proportional to the size of the inclusion, and a color of the graphics element being correlated to the chemical composition of the inclusion.

8 Claims, 2 Drawing Sheets

COUNTING INCLUSIONS IN ALLOYS BY IMAGE ANALYSIS

The present invention relates to a method of counting and analyzing inclusions in an alloy by image analysis.

Certain alloys may present inclusions, where an inclusion is defined as being a microscopic particle of chemical composition that is different from the composition of the alloy. Such inclusions are found in undesirable manner in the mass of an alloy. They are induced by the method of melting used for preparing the material. Such inclusions act as places where stresses are concentrated. They may serve to initiate microcracks that progress as fatigue. The chemical composition, the quantity, the size, and the spatial distribution of inclusions are parameters that have an influence on fatigue behavior. Consequently, it is essential to be able to count and classify the inclusions present in a given alloy. Furthermore, such metallurgical analysis needs to be performed on samples that are representative of a part (dimensions that are sufficiently great and the same transformation state).

Present methods of counting inclusions in alloys such as steels consist in observing a micrographic section in an optical microscope and in comparing the inclusions that are observed with reference images showing different cases of inclusion present. That method presents several drawbacks: comparing with images lacks accuracy (there is bias that depends on the observer), and no information can be obtained concerning the chemical composition of the inclusions. It is therefore necessary to observe a large number of samples in order to be in a position to determine the inclusion cleanliness of the alloy. The method is thus laborious and painstaking (manual operation), and furthermore it is incomplete.

The invention seeks to propose a metallurgical analysis method that makes it possible in satisfactory manner to characterize the inclusion population of any alloy. It thus consists in determining the quantity, the size, the spatial distribution, and the chemical compositions of the inclusions present in the alloy, and then in combining such measurements as easily and as accurately as possible in order to obtain production savings while analyzing the alloy for inclusion cleanliness.

This object is achieved by the fact that the method comprises:

a) preparing a sample of the alloy;

b) determining inclusion detection thresholds by observation, with magnification, of at least one field of the sample;

c) detecting inclusions of the sample as a function of the threshold defined in step b), and counting the inclusions;

d) acquiring images of each of the inclusions detected in step c) and determining the size of each of the inclusions;

e) determining the chemical composition of each of the detected inclusions by chemically analyzing each of them; and f) making a map of the sample from the images acquired in step d), the map showing the spatial distribution of the inclusions, in which each of the detected inclusions is represented by a graphics element, the size of the graphics element being proportional to the size of the inclusion, and the color of this graphics element being correlated to the chemical composition of the inclusion.

By means of these provisions, all of the parameters needed for counting and analyzing the inclusions are measured on a sample that is selected to be sufficiently large to be statistically representative of the alloy, and the data acquired is combined optimally to obtain a map of the inclusions that is as complete and as easy and practical to use as possible, thereby achieving productivity savings. In particular, the map makes it possible to determine whether the inclusions are grouped together so as to form clusters of a general shape that is likely to give rise to stress concentration, which would be harmful to the fatigue strength of the alloy.

Advantageously, the method of counting and analyzing inclusions includes, after step f), the following step:

g) using the map of the detected inclusions made in step f) to analyze the sample as a function of at least one predetermined criterion.

This analysis of the sample using the map makes it possible to verify whether or not the alloy from which the sample was taken is in compliance.

The invention also provides a system for counting and analyzing the inclusions in an alloy.

According to the invention, the system comprises: a microscope; first means suitable for controlling the microscope, for detecting, as a function of detection thresholds, the inclusions present in a sample of the alloy and for counting the inclusions; chemical analysis apparatus suitable for obtaining chemical data from each of the inclusions; second means suitable for acquiring an image of each of the inclusions and for controlling the chemical analysis apparatus to determine the chemical composition thereof from the chemical data; third means suitable for making a map of the sample showing the spatial distribution of the inclusions in which each of the detected inclusions is represented by a graphics element, the size of the graphics element being proportional to the size of the inclusion, and the color of the graphics element being correlated to the chemical composition of the inclusion; and a device for displaying the map.

The invention can be well understood and its advantages appear better on reading the following detailed description of an embodiment given by way of non-limiting example. The description refers to the accompanying drawings, in which.

Figure 1:
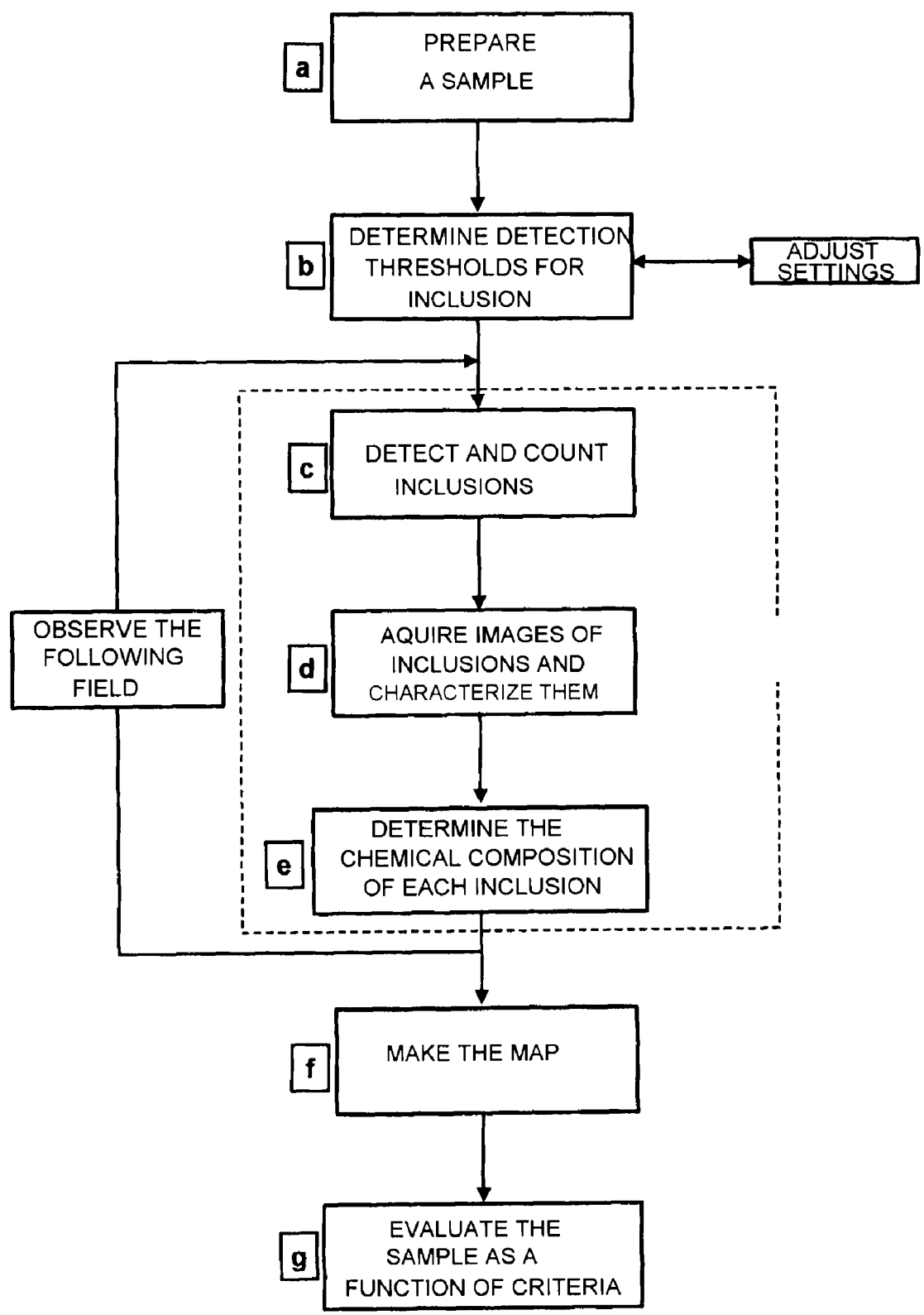
FIG. 1 shows the steps of the method of the invention.

The method of the invention is described below with reference to FIG. 1, which shows a sequence of steps in the method.

Analysis performed using an electron microscope, an energy dispersion microanalysis system, and various software means.

In step a), a sample of alloy for study is taken and the sample is prepared using known techniques. The preparation comprises polishing the surface of the sample to enable it to be observed by microscope. The microscope used is a scanning electron microscope (SEM). Greater magnification can be obtained with an SEM than with an optical microscope. Furthermore, observing the backscattered electrons of the SEM makes it possible to obtain better gray-scale contrast between inclusions and the matrix of the alloy.

When using SEM, the sample is polished in a manner that includes finishing polishing on a sheet impregnated with 1 micrometer ($\mu$m) diamonds, and then the sample is covered in a gold/palladium conductive film, e.g. deposited using a metal plater after passing through an ultrasound vessel for cleaning. The sample as prepared in this way is placed in the chamber of the SEM.

The sample is subdivided into fields, and each field is analyzed.

A certain number of microscope input parameters need to be set before starting analysis. These are the following parameters in particular:
- magnification;
- size of the acquired image (pixels);
- number of fields to be analyzed; and
- distribution of the fields.

The magnification of the microscope defines the size of a field, i.e. the dimensions of the area that is examined. This magnification lies in the range 100 to 500, since otherwise the time required to analyze each field is too long.

The size of each image acquired by the microscope is expressed in pixels, with one image corresponding to one field. By way of example, this size may be 512×512 pixels. The real size of the image depends on the magnification. The smallest statistically valid size for a sample is about 160 square millimeters ($mm^2$). Magnification and size are selected in such a manner that each inclusion has a size of at least 10 pixels.

The number of fields to be analyzed defines the total area of the observed sample.

For ease of operation, this sample surface is scanned in such a manner that the next field to be analyzed is adjacent to the field currently being analyzed. The distribution of fields is thus continuous.

In step b), a plurality of inclusion detection thresholds are set.

Thus, the inclusion size threshold and the gray level are selected to determine whether a zone of a certain size having a gray level that is different from that of the background corresponds to an inclusion that should be analyzed.

Furthermore, chemical composition thresholds are selected as a function of the nature of the alloy under examination. A list of elements that are likely to be present in the inclusions is selected and concentration ranges (thresholds) are selected for each of those elements. Since the stoichiometry of an inclusion is not known in advance, and since it is possible for there to be chemical interaction between the matrix and an inclusion, it is necessary to use concentration ranges. Such ranges are established by averaging the chemical analysis results that are obtained and the sizes of the inclusions that are observed during prior analysis and observation performed on 10 to 20 fields of the alloy.

As a minimum, the detection thresholds comprise a minimum concentration for at least one chemical element in an inclusion.

The above selection of parameters (thresholds) is generally accompanied by adjusting settings of the microscope and of the chemical analysis apparatus, as mentioned above.

In step c), inclusions are detected. This detection is performed using first software means $L_1$ for analyzing images and counting particles, e.g. Aphélion® software (from the supplier ADCIS) that includes a software package suitable for counting particles. These first software means $L_1$ detect inclusions for analysis (by binarizing the image), while using the size and gray level thresholds defined in step b), and they count all of the inclusions.

In parallel with this detection operation, the first software means $L_1$ control the microscope so as to scan each field.

In step d), the first software means $L_1$ control second software means $L_2$ for image acquisition and chemical analysis. The second software means $L_2$ acquire an image of the field, which image is subsequently transmitted to the first software means $L_1$ in order to characterize the shape (outline), the size (dimension), and the position within the field of each insertion detected in step c) by the first software means $L_1$. By way of example, the second software means $L_2$ are Spirit® software (supplier Synergie4/PGT).

Figure 2:
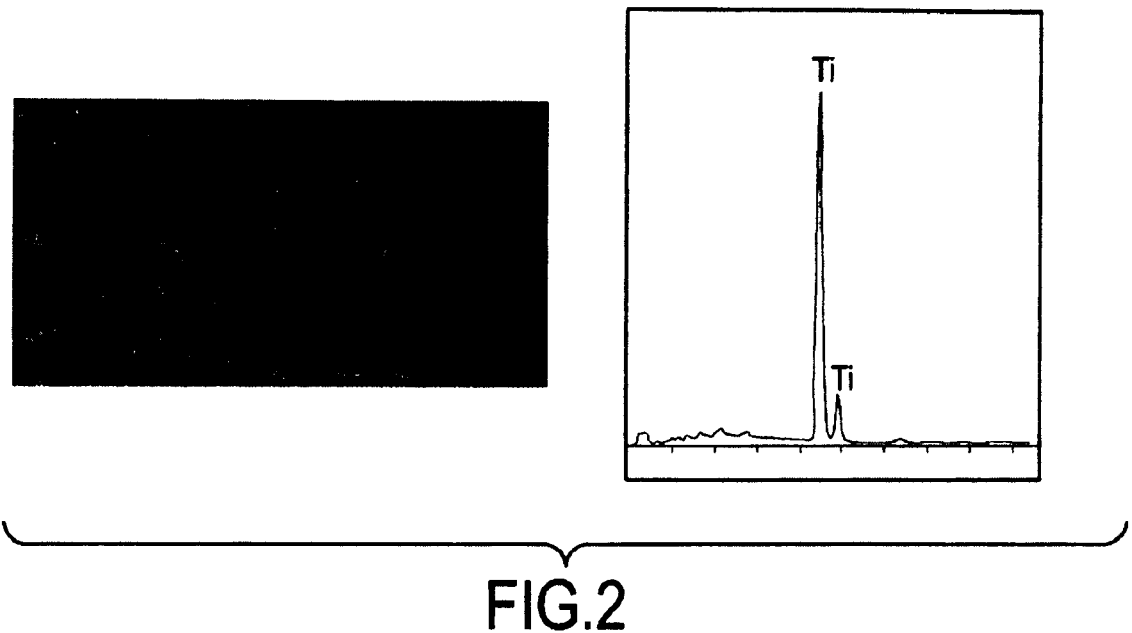
FIG. 2 is an image of an inclusion in an alloy together with the result of chemical analysis thereof as performed by the method of the invention.

The left-hand portion of FIG. 2 is an image of a portion of the field, showing an inclusion (in black on a gray background).

In step e), the second software means $L_2$ control a chemical analyzer apparatus using the data supplied to $L_2$ by $L_1$ in step d) concerning the positions of inclusions. This data enables $L_2$ to perform a chemical analysis of each detected inclusion and to determine the percentage of each identified element in each inclusion. The results are transmitted to the first software means $L_1$, which give the chemical composition of each inclusion by using the concentration thresholds selected in step b) for each of the preselected characteristic chemical elements. For example, the chemical analysis apparatus may be a spectrometer. The spectrometer is preferably an energy dispersion microanalysis system. The spectrometer is coupled to the scanning electron microscope (SEM).

The right-hand portion of FIG. 2 shows the results of the mechanical analysis of the inclusion in the image shown in the left-hand portion of FIG. 2. There can clearly be seen the concentration peak corresponding to the element titanium, Ti, thus making it possible to identify the inclusion as being titanium nitride.

Steps b) to e) are repeated for each of the fields covering a portion of the surface of the sample, until the entire surface of the sample has been analyzed.

In step f), third software means $L_3$ make a map of the sample on the basis of the images of all of the fields of the sample, together with the data recovered by the first software $L_1$ and the second software $L_2$ and transferred to the third software means $L_3$.

In this map, each of the detected inclusions is represented by a graphics element, the size of the graphics element being proportional to the size of the inclusion. A color is arbitrarily associated with each type of inclusion as a function of its chemical composition, as determined in step e).

A display device, e.g. a screen, then serves to display the resulting map.

Once the map has been obtained, the method may include an additional step of evaluating the validity of the analysis of the sample on the basis of certain criteria.

This additional step, step g) in FIG. 1, is performed manually by an operator. This step corresponds to a validity test: if the test is positive, the analysis is deemed to be valid, and its results are usable. Otherwise the analysis is deemed to be invalid; it is not retained and other analyses need to be performed after modifying certain input parameters.

By way of example, the following data is recovered from the map: the number of detected inclusions, the spatial distribution of the inclusions, the size of the inclusions.

There follows an example of a Maraging 250 steel including nitride inclusions and other inclusions.

For the nitride inclusions, providing their distribution is uniform, the maximum dimension of the inclusions must be less than 20 μm, and the number of inclusions per field having an area of 0.5 $mm^2$ must be less than or equal to 4, and possibly lying in the range 4 to 16 in a single one of the fields. If the inclusions are in alignment or grouped together in a cluster, the maximum size of such a cluster or alignment should be less than 75 μm, with the number of such clusters or alignments being no greater than one per 0.5 $mm^2$ field, and their thickness must be less than 0.9 μm.

Concerning the other inclusions, providing their spatial distribution is uniform, the maximum dimension of the inclusions must be less than 20 μm, and the number of inclusions per 0.5 $mm^2$ field must be less than or equal to 4. If the inclusions are in alignment or grouped together in clusters, the maximum dimension of such a cluster or alignment must be less than 75 μm, with the number of clusters for alignment being no greater than one per 0.5 $mm^2$ field, and their thickness must be less than 9 μm.

The invention also provides a system for counting and analyzing inclusions in an alloy by using the above-described method, i.e. a system comprising: a microscope; first software means $L_1$ suitable for controlling the microscope, for detecting the inclusions present on a sample of the alloy as a function of detection thresholds, and for counting the inclusions; chemical analysis apparatus suitable for obtaining chemical data from each of the inclusions; second software means $L_2$ suitable for acquiring an image of each of the inclusions and for controlling the chemical analysis apparatus to determine the chemical composition thereof on the basis of the chemical data; and third software means $L_3$ suitable for making a map of the sample in which each detected inclusion is represented by a graphics element of size proportional to the size of the inclusion, and of a color that is correlated to the chemical composition of the inclusion. The system also includes a device for displaying the map.

All metal alloys are suitable for being examined by the above-described system for counting and analyzing inclusions. Such alloys may be an optionally alloy steel, a nickel-based alloy, a cobalt-based alloy, an alloy prepared by powder metallurgy.

There follow examples in which the method of the invention was applied to Maraging 250 steels.

EXAMPLE

Maraging 250 Steel X2NiCoMo18-8-5

The input parameters were as follows:
magnification: 200;
acquired image size (pixels): 512×512;
number of fields to be analyzed: 600;
field distribution: continuous.
The detection thresholds for inclusions were as follows:
inclusion size threshold: 5 µm;
gray level thresholds: 190 to 250;
chemical composition thresholds: see Table I below.

TABLE I

|    | Oxides | | Sulfides | | Oxysulfides | | Titanium nitrides | |
|----|---|---|---|---|---|---|---|---|
|    | Min | Max | Min | Max | Min | Max | Min | Max |
| Fe | 0.0 | 68.4 | 0.0 | 68.4 | 0.0 | 68.4 | 0.0 | 68.4 |
| O  | 1.0 | 100.0 | 0.0 | 1.0 | 1.0 | 3.0 | 0.0 | 100.0 |
| Mg | 0.0 | 100.0 | 0.0 | 100.0 | 0.0 | 100.0 | 0.0 | 100.0 |
| Al | 0.0 | 100.0 | 0.0 | 100.0 | 0.0 | 100.0 | 0.0 | 100.0 |
| Ca | 0.0 | 100.0 | 0.0 | 100.0 | 0.0 | 100.0 | 0.0 | 100.0 |
| Si | 0.0 | 100.0 | 0.0 | 100.0 | 0.0 | 100.0 | 0.0 | 100.0 |
| S  | 0.0 | 1.5 | 1.5 | 100.0 | 1.0 | 3.0 | 0.0 | 100.0 |
| Ti | 0.0 | 3.5 | 0.0 | 3.5 | 0.0 | 3.5 | 3.5 | 100.0 |
| Ni | 0.0 | 15.3 | 0.0 | 15.3 | 0.0 | 15.3 | 0.0 | 15.3 |
| Co | 0.0 | 6.3 | 0.0 | 6.3 | 0.0 | 6.3 | 0.0 | 6.3 |
| Mn | 0.0 | 100.0 | 0.0 | 100.0 | 0.0 | 100.0 | 0.0 | 100.0 |
| Mo | 0.0 | 100.0 | 0.0 | 100.0 | 0.0 | 100.0 | 0.0 | 100.0 |

The chemical analysis results show that the inclusions present in the alloy were as follows:
type 1 inclusions: titanium nitrides;
type 2 inclusions: oxides;
type 3 inclusions: sulfides.

Figure 3:
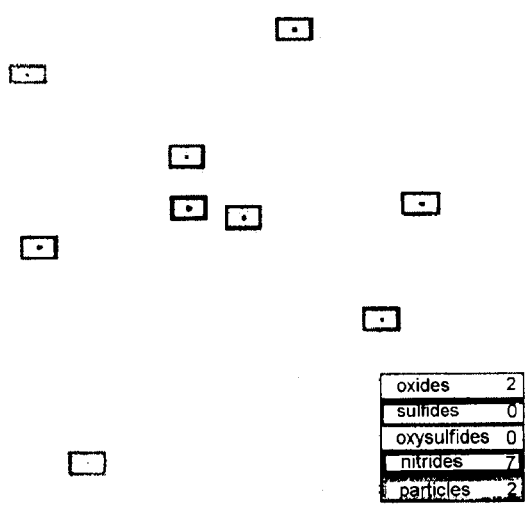
FIG. 3 is a map showing inclusions in Maraging 250 steel, as obtained by a method of the invention.

FIG. 3 shows the inclusion map obtained for the analyzed sample.

The invention claimed is:

1. A method of counting and analyzing inclusions in an alloy by image analysis, the method comprising:

a) preparing a sample of the alloy;
b) determining inclusion detection thresholds by observation, with magnification, of at least one field of the sample;
c) detecting inclusions of the sample as a function of the threshold defined in the determining b), and counting the inclusions;
d) acquiring images of each of the inclusions detected in the detecting c) and determining a size of each of the inclusions;
e) determining the chemical composition of each of the detected inclusions by chemically analyzing each of the detected inclusions; and
f) making a map of the sample from the images acquired in the acquiring d), the map showing spatial distribution of the inclusions, in which each of the detected inclusions is represented by a graphics element, a size of the graphics element being proportional to the size of the inclusion, and a color of the graphics element being correlated to the chemical composition of the inclusion.

2. A method of counting and analyzing inclusions according to claim 1, wherein in the determining b), the detection thresholds comprise a minimum dimension for an inclusion, and a minimum concentration of at least one chemical element in an inclusion.

3. A method of counting and analyzing inclusions according to claim 1, further comprising, after the making f):
g) using the map of the detected inclusions to analyze the sample as a function of at least one predetermined criterion.

4. A method of counting and analyzing inclusions according to claim 3, wherein each criterion is selected from: distribution of the inclusions; dimensions of each inclusion; and number of inclusions per unit area.

5. A method of counting and analyzing inclusions according to claim 1, wherein the alloy is selected from: a carbon steel; a nickel-based alloy; a cobalt-based alloy; an alloy produced by powder metallurgy.

6. A system for counting and analyzing inclusions in an alloy, the system comprising:
a microscope;
first means for controlling the microscope, for detecting, as a function of detection thresholds, inclusions present in a sample of the alloy and for counting the inclusions;
a chemical analysis apparatus configured to obtain chemical data from each of the inclusions;
second means for acquiring an image of each of the inclusions and for controlling the chemical analysis apparatus to determine the chemical composition thereof from the chemical data;
third means for making a map of the sample showing spatial distribution of the inclusions in which each of the detected inclusions is represented by a graphics element, a size of the graphics element being proportional to a size of the inclusion, and a color of the graphics element being correlated to the chemical composition of the inclusion; and
a device for displaying the map.

7. A system according to claim 6, wherein the detection thresholds comprise: a minimum dimension for an inclusion; and a minimum concentration of at least one chemical element in an inclusion.

8. A system according to claim 6, wherein the microscope is a scanning electron microscope, and the chemical analysis appliance is an energy dispersion microanalysis system.

* * * * *